United States Patent
Yamamoto (10) Patent No.: US 10,238,366 B2
(45) Date of Patent: Mar. 26, 2019

(54) ULTRASOUND DIAGNOSTIC APPARATUS

(71) Applicant: FUJIFILM CORPORATION, Tokyo (JP)

(72) Inventor: Katsuya Yamamoto, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 923 days.

(21) Appl. No.: 14/800,432

(22) Filed: Jul. 15, 2015

(65) Prior Publication Data

US 2015/0313576 A1 Nov. 5, 2015

Related U.S. Application Data

(63) Continuation of application No. PCT/JP2014/050555, filed on Jan. 15, 2014.

(30) Foreign Application Priority Data

Jan. 16, 2013 (JP) .................................. 2013-005410

(51) Int. Cl.
*A61B 8/00* (2006.01)
*A61B 8/08* (2006.01)
(Continued)

(52) U.S. Cl.
CPC ............ *A61B 8/4494* (2013.01); *A61B 8/145* (2013.01); *A61B 8/5207* (2013.01);
(Continued)

(58) Field of Classification Search
CPC ......... A61B 8/00; A61B 8/4494; A61B 8/145; A61B 8/5207; A61B 8/5346;
(Continued)

(56) References Cited

U.S. PATENT DOCUMENTS

2013/0018266 A1* 1/2013 Nishikubo ........... A61B 8/4483
600/443

FOREIGN PATENT DOCUMENTS

JP 2010-201120 A 9/2010
WO WO 2008/010509 A1 1/2008

OTHER PUBLICATIONS

International Search Report, issued in PCT/JP2014/050555, dated Feb. 25, 2014.
(Continued)

*Primary Examiner* — Carolyn A Pehlke
(74) *Attorney, Agent, or Firm* — Birch, Stewart, Kolasch & Birch, LLP (57) ABSTRACT

An ultrasound diagnostic apparatus includes: a transducer array; a transmission circuit transmitting an ultrasonic beam from the transducer array; a reception circuit obtaining fundamental component data based on reception signals corresponding to the fundamental component of an ultrasonic wave and harmonic component data based on reception signals corresponding to a harmonic component of the ultrasonic wave; and an image producer performing frame correlation processing on the fundamental component data and the harmonic component data generated for each frame so as to produce an ultrasound image. The frame correlation processing is performed such that the weight of harmonic component data of another frame used in the frame correlation processing of the harmonic component data is greater than the weight of fundamental component data of another frame used in the frame correlation processing of the fundamental component data.

11 Claims, 3 Drawing Sheets

(51) Int. Cl.
*A61B 8/14* (2006.01)
*B06B 1/06* (2006.01)
*G01S 7/52* (2006.01)

(52) U.S. Cl.
CPC .......... *A61B 8/5246* (2013.01); *B06B 1/0611* (2013.01); *G01S 7/52038* (2013.01); *A61B 8/5269* (2013.01)

(58) Field of Classification Search
CPC ... A61B 8/5269; A61B 8/4477; A61B 8/4483; A61B 8/4488; A61B 8/52; A61B 8/5215; B06B 1/0611; G01S 7/52038; G06T 7/0012
See application file for complete search history.

(56) References Cited

OTHER PUBLICATIONS

Translation of the International Preliminary Report on Patentability and Written Opinion of the International Searching Authority (Forms PCT/IB/373 and PCT/ISA/237), dated Jul. 30, 2015, for International Application No. PCT/JP2014/050555.

* cited by examiner

ULTRASOUND DIAGNOSTIC APPARATUS

CROSS-REFERENCE TO RELATED APPLICATIONS

This application is a continuation of PCT International Application No. PCT/JP2014/050555 filed on Jan. 15, 2014, which claims priority under 35 U.S.C. § 119(a) to Japanese Patent Application No. 2013-005410 filed on Jan. 16, 2013. Each of the above applications is hereby expressly incorporated by reference, in its entirety, into the present application.

BACKGROUND OF THE INVENTION

The present invention relates to an ultrasound diagnostic apparatus, and in particular, to an ultrasound diagnostic apparatus which performs transmission and reception of ultrasonic waves using a plurality of inorganic piezoelectric elements and a plurality of organic piezoelectric elements.

Conventionally, in the medical field, an ultrasound diagnostic apparatus using ultrasound images has been put to practical use. Generally, in this type of ultrasound diagnostic apparatus, an ultrasonic beam is transmitted toward the inside of a subject from an ultrasound probe, an ultrasonic echo from the subject is received by the ultrasound probe, and a signal of such reception is electrically processed, thereby producing an ultrasound image.

In recent years, in order to perform more accurate diagnosis, there has been an attempt to use harmonic imaging in which harmonic components generated by the distortion of an ultrasonic waveform due to nonlinearity of a subject are received and imaged. For example, in an ultrasound diagnostic apparatus disclosed in JP 2010-201120 A, it has been suggested that a reception signal obtained from an ultrasound probe and a delay signal obtained by delaying the phase of the reception signal using an analog delay circuit are added to remove a fundamental component from the reception signal and extract a harmonic component. An ultrasound image which accurately reflects the inside of the subject can be produced by the extracted harmonic components.

As an ultrasound probe suitable for harmonic imaging, for example, as disclosed in WO 2008/010509 A, an ultrasound probe which is formed by laminating an inorganic piezoelectric element and an organic piezoelectric element has been suggested. An organic piezoelectric substance which is used for the organic piezoelectric element responds to harmonic components of ultrasonic waves with high sensitivity, and by transmitting high-power ultrasonic beams from the inorganic piezoelectric element of the ultrasound probe, the harmonic components can be received by the organic piezoelectric element. Furthermore, fundamental components having an excellent S/N ratio can also be received by the inorganic piezoelectric element. In this way, reception signals having different properties from each other are obtained from the inorganic piezoelectric element and the organic piezoelectric element, and an ultrasound image suitable for diagnosis can be produced by adding a high-definition ultrasound image produced based on the reception signals from the organic piezoelectric element to an ultrasound image having an excellent S/N ratio and produced based on the reception signal from the inorganic piezoelectric element.

However, the organic piezoelectric substance of the organic piezoelectric element has electric capacitance smaller than that of the inorganic piezoelectric substance of the inorganic piezoelectric element. In general, intensity N of noise caused by a piezoelectric element out of noise included in a reception signal is expressed by Equation (1), and is increased as the electric capacitance C of the piezoelectric substance becomes smaller. Herein, k represents a Boltzmann constant, and T represents temperature (K).

$$N = \sqrt{k \cdot T / C} \quad (1)$$

That is, a larger amount of noise of higher intensity is included in the reception signal output from the organic piezoelectric element compared to the reception signal output from the inorganic piezoelectric element, and thus a large amount of noise of high intensity is included in the ultrasound image produced based on the reception signals output from the organic piezoelectric elements. For this reason, although the ultrasound image produced based on the reception signals from the inorganic piezoelectric elements has an excellent S/N ratio, there is a problem in that, if the ultrasound image produced based on the reception signals from the organic piezoelectric elements is added thereto, the noise of high intensity included in the added ultrasound image is reflected, and the image quality of the resulting ultrasound image is unnecessarily deteriorated.

SUMMARY OF THE INVENTION

The present invention has been accomplished in order to solve the aforementioned problems in the prior art, and an object thereof is to provide an ultrasound diagnostic apparatus capable of suppressing deterioration of image quality of an ultrasound image when adding an ultrasound image produced by reception signals from a plurality of organic piezoelectric elements to an ultrasound image produced by reception signals from a plurality of inorganic piezoelectric elements.

An ultrasound diagnostic apparatus according to the present invention comprises:

a transducer array having a plurality of inorganic piezoelectric elements and a plurality of organic piezoelectric elements;

a transmission circuit configured to transmit an ultrasonic beam from the transducer array toward a subject;

a reception circuit configured to obtain fundamental component data by processing reception signals corresponding to a fundamental component of an ultrasonic wave output from the inorganic piezoelectric elements, and obtain harmonic component data by processing reception signals corresponding to a harmonic component of the ultrasonic wave output from the organic piezoelectric elements, upon reception of an ultrasonic echo from the subject by the transducer array; and an image producer configured to perform frame correlation processing on the fundamental component data and the harmonic component data generated by the reception circuit for each frame by using the fundamental component data and the harmonic component data of another frame, respectively, so as to produce a correlation processing image of the fundamental component and a correlation processing image of the harmonic component, and add the correlation processing image of the fundamental component and the correlation processing image of the harmonic component to each other so as to produce an ultrasound image in which the fundamental component and the harmonic component are combined together, wherein the image producer performs the frame correlation processing on the fundamental component data and the harmonic component data of a frame such that weight of the harmonic component data of another frame in the frame correlation processing of the harmonic component data is greater than weight of the fundamental component data of another frame in the frame correlation processing of the fundamental component data.

DETAILED DESCRIPTION OF THE INVENTION

Hereinafter, embodiments of the present invention will be described referring to the accompanying drawings.

Embodiment 1

Figure 1:
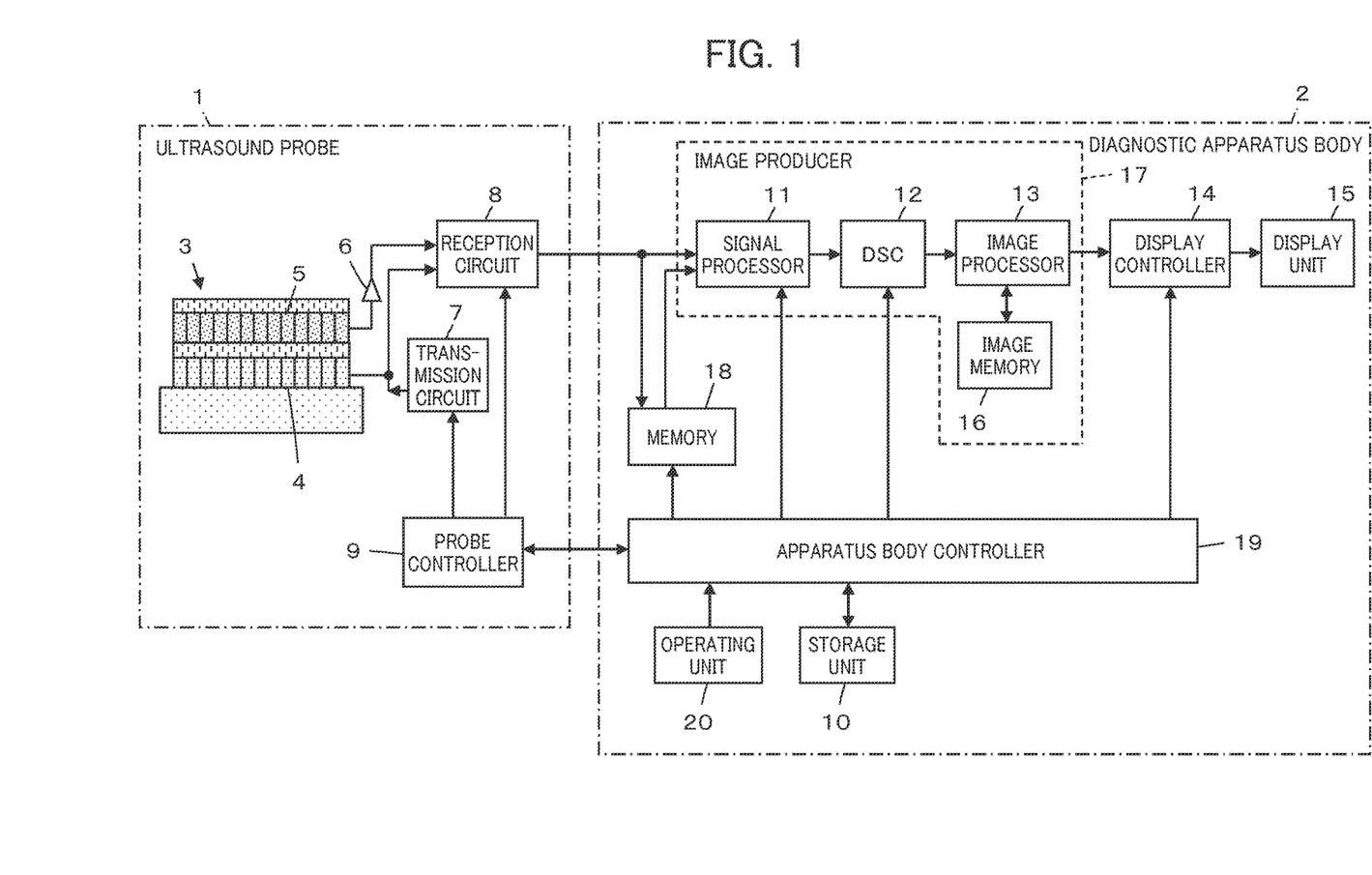
FIG. 1 is a block diagram showing the configuration of an ultrasound diagnostic apparatus according to Embodiment 1 of the present invention.

FIG. 1 shows the configuration of an ultrasound diagnostic apparatus according to Embodiment 1. The ultrasound diagnostic apparatus includes an ultrasound probe 1, and a diagnostic apparatus body 2 connected to the ultrasound probe 1.

The ultrasound probe 1 has a laminated transducer array 3. The laminated transducer array 3 has a plurality of inorganic piezoelectric elements 4 which are arranged in array form, and a plurality of organic piezoelectric elements 5 which are formed and laminated on the inorganic piezoelectric elements 4 and are arranged in array form. A corresponding preamplifier 6 is connected to each of the organic piezoelectric elements 5.

A transmission circuit 7 and a reception circuit 8 are each connected to the inorganic piezoelectric elements 4, and the reception circuit 8 is connected to the preamplifiers 6 as connected to the organic piezoelectric elements 5. Furthermore, a probe controller 9 is connected to the transmission circuit 7 and the reception circuit 8.

The diagnostic apparatus body 2 has a signal processor 11 connected to the reception circuit 8 of the ultrasound probe 1. A digital scan converter (DSC) 12, an image processor 13, a display controller 14, and a display unit 15 are sequentially connected to the signal processor 11. An image memory 16 is connected to the image processor 13, and an image producer 17 is constituted of the signal processor 11, the DSC 12, the image processor 13, and the image memory 16. The diagnostic apparatus body 2 also has a memory 18 which is connected to the reception circuit 8 of the ultrasound probe 1 and to the signal processor 11 as well, and an apparatus body controller 19 is connected to the signal processor 11, the DSC 12, the display controller 14, and the memory 18.

Furthermore, an operating unit 20 and a storage unit 10 are each connected to the apparatus body controller 19.

The probe controller 9 of the ultrasound probe 1 and the apparatus body controller 19 of the diagnostic apparatus body 2 are connected with each other.

The inorganic piezoelectric elements 4 of the laminated transducer array 3 can be used as elements for both transmission and reception of ultrasonic waves. Each of the inorganic piezoelectric elements 4 transmits ultrasonic waves according to driving signals supplied from the transmission circuit 7, and outputs reception signals obtained by receiving an ultrasonic echo from a subject to the reception circuit 8. The organic piezoelectric elements 5 of the laminated transducer array 3 are used as elements exclusively for reception of ultrasonic waves, and output reception signals obtained by receiving an ultrasonic echo from the subject to the reception circuit 8 through the preamplifiers 6.

Each of the inorganic piezoelectric elements 4 is a transducer in which electrodes are formed at both ends of an inorganic piezoelectric body composed of a piezoelectric ceramic represented by lead zirconate titanate (PZT) or a piezoelectric single crystal represented by a lead magnesium niobate-lead titanate solid solution (PMN-PT).

Meanwhile, each of the organic piezoelectric elements 5 is a transducer in which electrodes are formed at both ends of an organic piezoelectric body composed of a piezoelectric polymer, such as polyvinylidene fluoride (PVDF) or a polyvinylidene fluoride-trifluoroethylene copolymer.

When a pulsed or continuous-wave voltage is applied across the electrodes of each of the inorganic piezoelectric elements 4, the inorganic piezoelectric bodies of the elements expand and contract to generate pulsed or continuous-wave ultrasonic waves, and these ultrasonic waves are combined into an ultrasonic beam.

When the ultrasonic echo enters the laminated transducer array 3, the inorganic piezoelectric body of each of the inorganic piezoelectric elements 4 expands and contracts in response to the fundamental component of the ultrasonic wave, and an electrical signal is generated and output as a reception signal. Furthermore, the organic piezoelectric body of each of the organic piezoelectric elements 5 expands and contracts in response to a harmonic component of the ultrasonic wave with high sensitivity, and an electrical signal is generated and output as a reception signal. The reception signal output from the organic piezoelectric element 5 is amplified by the corresponding preamplifier 6 and then input to the reception circuit 8.

The transmission circuit 7 includes, for example, a plurality of pulsers. The transmission circuit 7 adjusts the delay amount of each of the driving signals based on a transmission delay pattern selected according to a control signal from the probe controller 9 such that ultrasonic waves transmitted from the inorganic piezoelectric elements 4 of the laminated transducer array 3 constitute an ultrasonic beam, and supplies the adjusted driving signals to the respective inorganic piezoelectric elements 4.

The reception circuit 8 amplifies the reception signals obtained by the respective inorganic piezoelectric elements 4 or the respective organic piezoelectric elements 5, then subjects them to AD conversion, and thereafter, performs reception focusing by giving a delay to each of the reception signals according to a sound speed or a distribution of the sound speed set based on a reception delay pattern selected according to a control signal from the probe controller 9, and adding the reception signals. By the reception focusing, sample data (sound ray signal) is generated in which the focus of the ultrasonic echo received by the inorganic piezoelectric elements 4 or the organic piezoelectric elements 5 is narrowed down. The sample data is generated for each frame based on the ultrasonic echo received sequentially by the inorganic piezoelectric elements 4 or the organic piezoelectric elements 5.

The probe controller 9 controls the respective sections of the ultrasound probe 1 based on various control signals transmitted from the apparatus body controller 19 of the diagnostic apparatus body 2.

The signal processor 11 of the diagnostic apparatus body 2 performs correction of attenuation due to distance on the sample data generated for each frame by the reception circuit 8 of the ultrasound probe 1, depending on the depth of the reflection position of the ultrasonic wave, and then performs envelope detection processing to sequentially generate B-mode image data which is tomographic image information relating to the tissue in the subject. Herein, the B-mode image data as generated includes image data of the fundamental components generated based on the reception signals from the inorganic piezoelectric elements 4, and image data of the harmonic components generated based on the reception signals from the organic piezoelectric elements 5.

The DSC 12 converts the B-mode image data of the fundamental components and the B-mode image data of the harmonic components generated by the signal processor 11 into image data suitable for the conventional television signal scanning mode (raster conversion).

The image processor 13 performs various necessary image processing, such as gradation processing, on the B-mode image data of the fundamental components and the B-mode image data of the harmonic components input from the DSC 12, and then stores both the B-mode image data in the image memory 16 for each frame. Subsequently, the image processor 13 reads the B-mode image data of the fundamental components and the B-mode image data of the harmonic components stored in the image memory 16, performs frame correlation processing thereon, and adds the B-mode image data of the harmonic components subjected to the frame correlation processing to the B-mode image data of the fundamental components also subjected to the frame correlation processing, thereby producing composite image data in which the fundamental components and the harmonic components are combined.

The display controller 14 causes the display unit 15 to display an ultrasound diagnostic image on the basis of the composite image data input from the image processor 13.

The display unit 15 includes, for example, a display device such as an LCD and displays an ultrasound diagnostic image under the control of the display controller 14.

The operating unit 20 allows an operator to perform input operations, and may be constituted of a keyboard, a mouse, a trackball, a touch panel or the like.

The storage unit 10 stores operation programs and the like, and a recording medium such as a hard disk, a flexible disk, an MO, an MT, a RAM, a CD-ROM, a DVD-ROM, an SD card, a CF card, and a USB memory or a server can be used as the storage unit 10.

The apparatus body controller 19 controls the respective constituents in the diagnostic apparatus body 2 on the basis of, for instance, various command signals input by the operator through the operating unit 20.

Herein, the signal processor 11, the DSC 12, the image processor 13, and the display controller 14 are embodied by a CPU and operation programs for causing the CPU to execute various processing operations, but these constituents may be embodied by a digital circuitry.

Next, the frame correlation processing which is performed on the image data of the fundamental components and the image data of the harmonic components in the image processor 13 will be described.

The S/N ratios of an ultrasound image of fundamental components produced based on the reception signals from the inorganic piezoelectric elements 4 and an ultrasound image of harmonic components produced based on the reception signals from the organic piezoelectric elements 5 are to be improved by the frame correlation processing. Herein, the frame correlation processing is processing in which noise unevenly generated between frames, for example, between a current image frame and a previous image frame (another frame), is reduced by averaging the image frames based on the correlation between the image frames, whereby producing an ultrasound image (correlation processing image) having an improved S/N ratio. For example, when the frame correlation processing is performed using a current image frame and two previous image frames, this can be expressed by $P = a \times T_n + b \times T_{n-1} + c \times T_{n-2}$. Herein, P represents a correlation processing image, $T_n$ represents a current image frame, $T_{n-1}$ represents a preceding image frame, and $T_{n-2}$ represents a second preceding image frame. In addition, a, b, and c respectively represent correlation coefficients, and can be expressed by $a + b + c = 1$.

As described above, since the electric capacitance of the organic piezoelectric elements 5 is smaller than the electric capacitance of the inorganic piezoelectric elements 4, a larger amount of noise of high intensity is included in the reception signals output from the organic piezoelectric elements 5 compared to the reception signals output from the inorganic piezoelectric elements 4.

Figure 2:
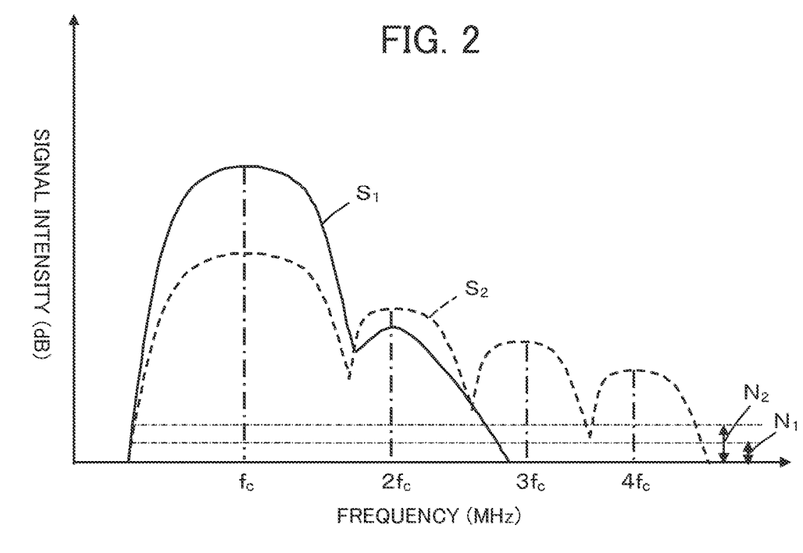
FIG. 2 is a graph showing intensity distributions of reception signals and noise therein obtained in an inorganic piezoelectric element and an organic piezoelectric element, respectively.

FIG. 2 shows an example of reception signals when an ultrasonic beam of a frequency $f_c$ is transmitted from the inorganic piezoelectric elements 4, and an ultrasonic echo from the subject is received by the inorganic piezoelectric elements 4 and the organic piezoelectric elements 5. As shown in FIG. 2, in the inorganic piezoelectric elements 4, a narrowband reception signal $S_1$ mainly composed of the fundamental component (frequency: $f_c$) is obtained. In contrast, in the organic piezoelectric elements 5, a broadband reception signal $S_2$ including harmonic components (frequency: $2f_c$, $3f_c$, $4f_c$, . . . ) is obtained. Furthermore, in the reception signal $S_1$ obtained in the inorganic piezoelectric elements 4, the signal intensity is high and the intensity of noise $N_1$ is low. In contrast, the reception signal $S_2$ obtained in the organic piezoelectric elements 5 is characterized in that the signal intensity is low and the intensity of noise $N_2$ is high.

For the above reason, the ultrasound image of the fundamental components produced based on the reception signal $S_1$ includes noise of low intensity, whereas the ultrasound image of the harmonic components produced based on the reception signal $S_2$ includes noise of high intensity. When the above frame correlation processing is equally performed on the ultrasound image of the fundamental components and the ultrasound image of the harmonic components which are different from each other in intensity of noise as described above, the S/N ratio of each of the ultrasound images is improved, but the difference of noise does not become drastically small, and accordingly, the correlation processing image of the fundamental components and the correlation processing image of the harmonic components are still different from each other in intensity of noise included therein. If a composite image in which fundamental components and harmonic components are combined is produced by performing addition of the correlation processing image of the fundamental components and the correlation processing image of the harmonic components which are different from each other in intensity of noise, an excellent S/N ratio of the correlation processing image of the fundamental components is reduced by the noise of high intensity included in the correlation processing image of the harmonic components.

Therefore, the image processor 13 does not perform equal frame correlation processing on the ultrasound image of the fundamental components and the ultrasound image of the harmonic components, but performs frame correlation processing thereon such that the weight of a previous frame in the frame correlation processing of the harmonic components becomes greater than the weight of the previous frame in the frame correlation processing of the fundamental components. With this, it is possible to cause the intensity of the noise included in the correlation processing image of the harmonic components to greatly approximate to the intensity of the noise included in the correlation processing image of the fundamental components, and to produce a composite image in which degradation of the S/N ratio is suppressed, by performing addition of the correlation processing image of the fundamental components and the correlation processing image of the harmonic components between which the difference in intensity of noise has been reduced.

Next, the operation of Embodiment 1 will be described.

First, an ultrasonic beam is emitted from the inorganic piezoelectric elements 4 into the subject according to the driving signals from the transmission circuit 7 of the ultrasound probe 1. The ultrasonic beam is distorted in waveform as it propagates through the subject, and includes not only the fundamental component but also harmonic components. As a result, a narrowband ultrasonic echo mainly composed of the fundamental component is received by the inorganic piezoelectric elements 4, a broadband ultrasonic echo including harmonic components is received by the organic piezoelectric elements 5, and reception signals are output from the inorganic piezoelectric elements 4 and the organic piezoelectric elements 5. The reception signals from the organic piezoelectric elements 5 which have received the harmonic components include detailed information which is not included in the reception signals from the inorganic piezoelectric elements 4, but, since the electric capacitance of the organic piezoelectric elements 5 is small, the reception signals therefrom include a large amount of noise of high intensity compared to the reception signals from the inorganic piezoelectric elements 4.

The reception signals output from the inorganic piezoelectric elements 4 are input to the reception circuit 8, and the reception signals output from the organic piezoelectric elements 5 are amplified by the preamplifiers 6, and then input to the reception circuit 8. The respective reception signals are subjected to digital processing and reception focusing by the reception circuit 8 to generate sample data, and image data of the fundamental components and image data of the harmonic components are generated based on the sample data by the image producer 17 of the diagnostic apparatus body 2. Specifically, the sample data of the fundamental components and the sample data of the harmonic components are respectively subjected envelope detection processing by the signal processor 11 of the image producer 17, and then, each sample data is input to the image processor 13 through the DSC 12 and subjected to image processing, such as gradation processing, by the image processor 13. The image data of the fundamental components and the image data of the harmonic components generated in this way are stored in the image memory 16 for each frame by the image processor 13.

Subsequently, the image processor 13 reads the image data of the fundamental components and the image data of the harmonic components stored in the image memory 16, and performs frame correlation processing between a current image frame and a previous image frame. At this time, the frame correlation processing is performed such that the weight of the previous image frame in the frame correlation processing of the harmonic components becomes greater than the weight of the previous image frame in the frame correlation processing of the fundamental components.

Specifically, the image processor 13 can make the weight of the previous image frame in the frame correlation processing of the harmonic components greater by making the number of previous frames used in the frame correlation processing of the harmonic components greater than that of previous frames used in the frame correlation processing of the fundamental components.

Figure 3:
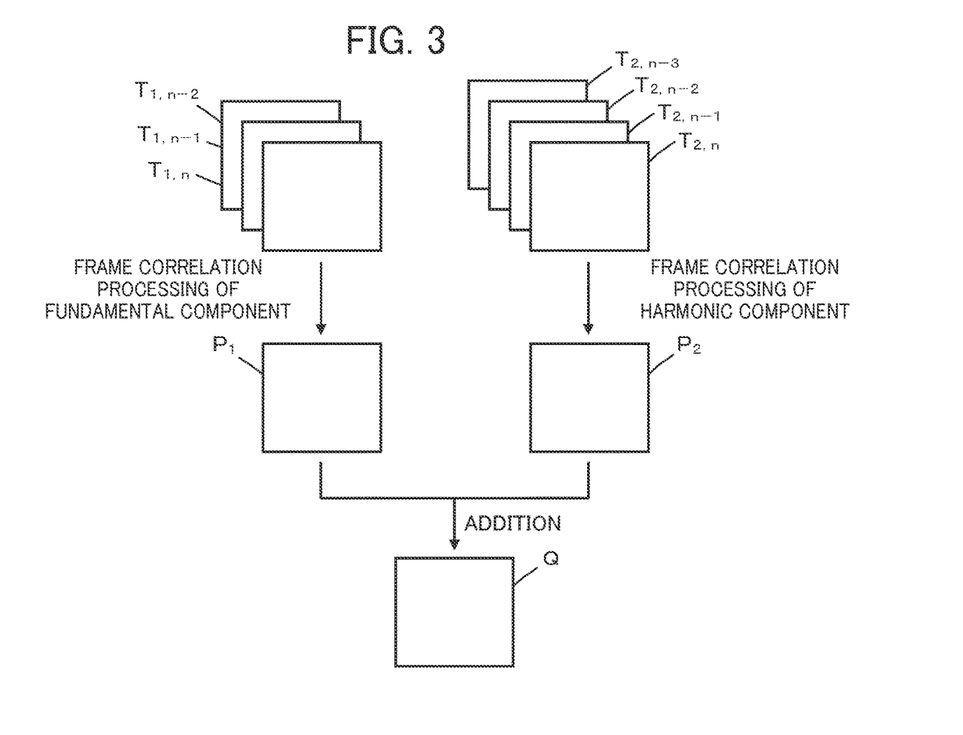
FIG. 3 is a diagram showing frame correlation processing which is performed on image data of fundamental components and image data of harmonic components, respectively.

For example, as shown in FIG. 3, on the image data of the fundamental components, frame correlation processing is performed between a current image frame $T_{1,n}$ and subsequent two previous image frames $T_{1,n-1}$ and $T_{1,n-2}$, and in contrast, on the image data of the harmonic components, frame correlation processing can be performed between a current image frame $T_{2,n}$ and subsequent three previous image frames $T_{2,n-1}$, $T_{2,n-2}$, and $T_{2,n-3}$. The frame correlation processing of the fundamental components can be expressed by Equation (2), and the frame correlation processing of the harmonic components can be expressed by Equation (3). Herein, $P_1$ represents a correlation processing image of fundamental components, and $P_2$ represents a correlation processing image of harmonic components. In addition, $a_1$, $b_1$, and $c_1$ respectively represent correlation coefficients of fundamental components, and can be set such that, for example, $a_1=0.70$, $b_1=0.20$, and $c_1=0.10$. Also, $a_2$, $b_2$, $c_2$, and $d_2$ respectively represent correlation coefficients of harmonic components, and can be set such that $a_2=0.67$, $b_2=0.20$, $c_2=0.10$, and $d_2=0.03$.

$$P_1 = a_1 \times T_{1,n} + b_1 \times T_{1,n-1} + c_1 \times T_{1,n-2} \tag{2}$$

$$P_2 = a_2 \times T_{2,n} + b_2 \times T_{2,n-1} + c_2 \times T_{2,n-2} + d_2 \times T_{2,n-3} \tag{3}$$

In this way, by making the weight of the previous image frame in the frame correlation processing of the harmonic components greater, it is possible to cause the intensity of the noise included in the correlation processing image $P_2$ of the harmonic components to approximate the intensity of the noise included in the correlation processing image $P_1$ of the fundamental components. Furthermore, it is possible to improve the S/N ratios of the correlation processing image $P_1$ of the fundamental components and the correlation processing image $P_2$ of the harmonic components with respect to the respective ultrasound images before the frame correlation processing.

Subsequently, the image processor 13 adds the correlation processing image $P_2$ of the harmonic components to the correlation processing image $P_1$ of the fundamental components, thereby producing a composite image Q in which the fundamental components and the harmonic components are combined.

The difference between the noise included in the correlation processing image $P_1$ of the fundamental components and the noise included in the correlation processing image $P_2$ of the harmonic components is greatly reduced by the frame correlation processing. Therefore, when adding the correlation processing image $P_2$ of the harmonic components, an excellent S/N ratio of the correlation processing image $P_1$ of the fundamental components is not greatly decreased, and thus, it is possible to produce the composite image Q in which high-definition harmonic components are combined with the fundamental components while maintaining the S/N ratio of fundamental components.

It is preferable for the image processor 13 to perform the frame correlation processing such that the intensity of the noise included in the correlation processing image $P_2$ of the harmonic components becomes almost the same as the intensity of the noise included in the correlation processing image $P_1$ of the fundamental components. Specifically, the frame correlation processing is preferably performed such that the ratio between the intensity of the noise included in the correlation processing image of the harmonic components and the intensity of the noise included in the correlation processing image of the fundamental components is within a range of ±6 dB, and the frame correlation processing is more preferably performed such that the ratio is within a range of ±3 dB. In this way, by making the intensities of the noises almost the same, it is possible to produce the composite image Q in which the correlation processing image $P_2$ of the harmonic components is combined with the correlation processing image $P_1$ of the fundamental components while maintaining an excellent S/N ratio of the correlation processing image $P_1$ of the fundamental components.

In the foregoing embodiment, the frame correlation processing is performed such that the number of previous frames used in the frame correlation processing of the harmonic components is greater than the number of previous frames used in the frame correlation processing of the fundamental components, to which the invention is not limited insofar as the weight of the previous frame in the frame correlation processing of the harmonic components is made greater than the weight of the previous frame in the frame correlation processing of the fundamental components.

Specifically, the correlation coefficient of another frame used in the frame correlation processing of the harmonic components can be set at a greater value than the correlation coefficient of another frame used in the frame correlation processing of the fundamental components. For example, the frame correlation processing of the fundamental components can be performed based on $P_1=0.70 \times T_{1,n}+0.20 \times T_{1,n-1}+0.10 \times T_{1,n-2}$, and the frame correlation processing of the harmonic components can be performed based on $P_2=0.50 \times T_{2,n}+0.30 \times T_{2,n-1}+0.20 \times T_{2,n-2}$.

In this way, the values of the correlation coefficient concerning the previous image frames $T_{2,n-1}$ and $T_{2,n-2}$ for the harmonic components are set to be greater than the values of the correlation coefficient concerning the previous image frames $T_{1,n-1}$ and $T_{1,n-2}$ for the fundamental components, whereby it is possible to make the weight of the previous image frame in the frame correlation processing of the harmonic components greater. Since the frame correlation processing is performed by changing the value of the correlation coefficient, it is not necessary to increase the number of frames for the harmonic components, and thus, it is possible to suppress an increase in load of the frame correlation processing.

The weight of the previous frame in the frame correlation processing of the harmonic components may be made greater by combining the above-described frame correlation processing operations, that is to say, by increasing the number of frames for the harmonic components and increasing the correlation coefficient of the previous image frame for the harmonic components.

While, in the foregoing embodiment, the frame correlation processing is performed on the image data of the fundamental components and the image data of the harmonic components as processed in the image processor 13, the frame correlation processing may be performed at any stage after the sample data is generated for each frame by the reception circuit 8, that is, after fundamental component data and harmonic component data are generated for each frame. For example, the frame correlation processing can be performed on the image data as processed by the signal processor 11, the DSC 12, or the like of the image producer 17.

In the foregoing embodiment, the frame correlation processing is performed between successive frames, to which the invention is not limited insofar as the S/N ratio of the ultrasound image can be improved. For example, the frame correlation processing can be performed between alternate frames.

Embodiment 2

Figure 4:
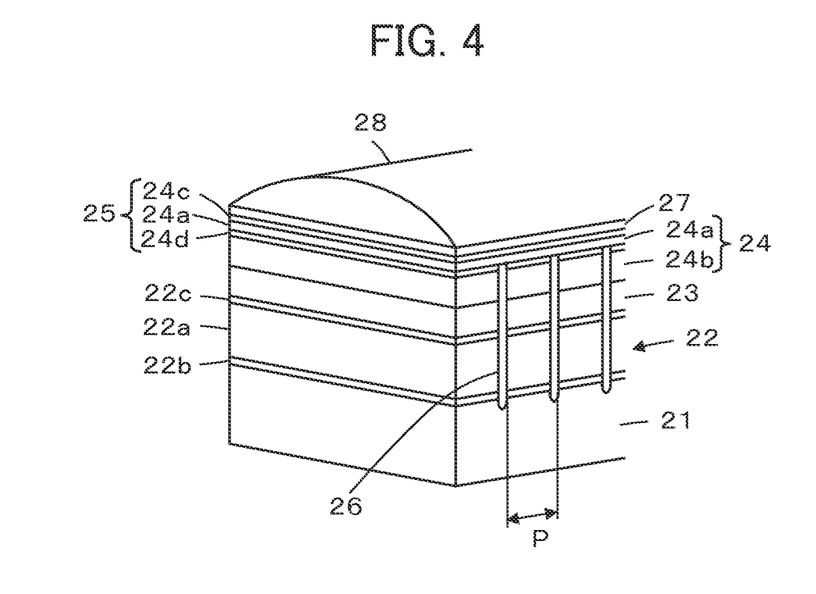
FIG. 4 is a perspective diagram showing the configuration of a laminated transducer array used in an ultrasound diagnostic apparatus according to Embodiment 2 of the present invention.
Figure 5:
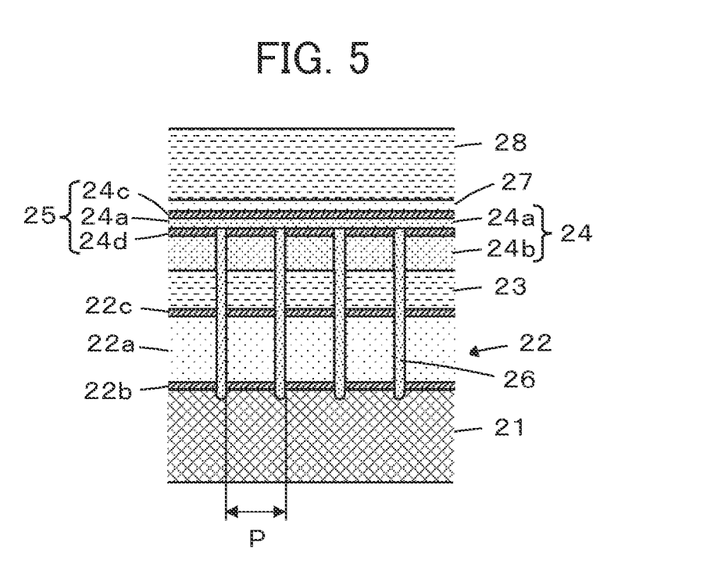
FIG. 5 is a cross-sectional diagram showing the configuration of the laminated transducer array used in the ultrasound diagnostic apparatus according to Embodiment 2.

FIGS. 4 and 5 show the configuration of a laminated transducer array which is used in an ultrasound diagnostic apparatus according to Embodiment 2.

A plurality of inorganic piezoelectric elements 22 are formed and arranged with a pitch P on the front surface of a backing material 21. The inorganic piezoelectric elements 22 have a plurality of inorganic piezoelectric bodies 22a separated from one another. A signal electrode layer 22b is bonded to one surface of each inorganic piezoelectric body 22a, and a ground electrode layer 22c is bonded to the other surface of the relevant inorganic piezoelectric body 22a. That is, each of the inorganic piezoelectric elements 22 is formed of the inorganic piezoelectric body 22a, the signal electrode layer 22b and the ground electrode layer 22c which are dedicated to the relevant element 22.

A first acoustic matching layer 23 is bonded onto the inorganic piezoelectric elements 22. The first acoustic matching layer 23 is divided into a plurality of fragments, and the fragments are arranged with the same pitch P as the inorganic piezoelectric elements 22.

Each of fragments constituting the inorganic piezoelectric elements 22 is preferably separated into a plurality of sub-fragments. For example, sub-dicing grooves extending in the lamination direction can be formed so that fragments constituting the inorganic piezoelectric bodies 22a, the signal electrode layers 22b and the ground electrode layers 22c (of the inorganic piezoelectric elements 22) or fragments constituting the inorganic piezoelectric bodies 22a, the signal electrode layers 22b, the ground electrode layers 22c and the first acoustic matching layer 23 may each be separated into a plurality of sub-fragments. Sub-dicing grooves extending in the lamination direction may also be formed so that fragments constituting the inorganic piezoelectric bodies 22a, the signal electrode layers 22b, the ground electrode layers 22c, the first acoustic matching layer 23 and a lower organic layer 24b may each be separated into a plurality of sub-fragments.

At this time, one or two sub-dicing grooves are preferably formed in each inorganic piezoelectric element 22 to divide the relevant element 22 into two or three pieces. In this way, the sub-dicing grooves are formed, whereby it is possible to improve the piezoelectric constant of the inorganic piezoelectric elements 22 and to improve transmission and reception sensitivity of the ultrasound probe.

A second acoustic matching layer 24 is bonded onto the first acoustic matching layer 23. The second acoustic matching layer 24 has two layers, namely, an upper organic layer 24a and the lower organic layer 24b.

The lower organic layer 24b is divided into a plurality of fragments, and the fragments are arranged on the first acoustic matching layer 23 with the same pitch P as the inorganic piezoelectric elements 22. The upper organic layer 24a has a sheet-like shape and extends over the entire lower organic layer 24b without being divided into a plurality of fragments. The sum of the thickness of the upper organic layer 24a and the thickness of the lower organic layer 24b is set such that desired acoustic matching can be performed with respect to the ultrasonic waves transmitted from the inorganic piezoelectric elements. For example, the sum of the thickness of the upper organic layer 24a and the thickness of the lower organic layer 24b is so set as to be in the vicinity of a thickness satisfying a $\lambda/4$ resonance condition with respect to the wavelength $\lambda$ of the fundamental wave (at the center frequency in the −6 dB band of maximum sensitivity of the inorganic piezoelectric bodies 22a) of the ultrasonic waves transmitted from the inorganic piezoelectric elements 22, whereby the second acoustic matching layer 24 composed of the upper organic layer 24a and the lower organic layer 24b can have an excellent acoustic transmissivity with respect to the ultrasonic waves transmitted from the inorganic piezoelectric elements 22.

Furthermore, the upper organic layer 24a constitutes a plurality of organic piezoelectric elements 25. That is, a ground electrode layer 24c is so bonded to the upper organic layer 24a as to extend over the front surface of the upper organic layer 24a, and a plurality of signal electrode layers 24d separated from one another with the same pitch P as the inorganic piezoelectric elements 22 are bonded to the rear surface of the upper organic layer 24a that faces the lower organic layer 24b. With this configuration, the upper organic layer 24a functions as an organic piezoelectric body for the organic piezoelectric elements 25. Each of the organic piezoelectric elements 25 formed and arranged in this way is constituted of the dedicated signal electrode layer 24d, as well as the upper organic layer 24a and the ground electrode layer 24c that are common to the organic piezoelectric elements 25. Accordingly, the arrangement pitch of the organic piezoelectric elements 25 is determined only by the arrangement pitch of the signal electrode layers 24d bonded onto the rear surface of the upper organic layer 24a, so that the organic piezoelectric elements 25 are arranged with the same pitch P as the inorganic piezoelectric elements 22.

The fragments of the respective strata of the transducer array, namely, the fragments of the inorganic piezoelectric elements 22, the first acoustic matching layer 23, the lower organic layer 24b of the second acoustic matching layer 24, and the signal electrode layers 24d, as separated in each stratum with the same pitch P, are positioned between respective strata to align them in the lamination direction, and the spaces between the respective alignments are filled with a filler to form separation parts 26 which separate the fragments of the respective strata, from the inorganic piezoelectric elements 22 up to the signal electrode layers 24d, from one another. That is, the separation parts 26 extend in the lamination direction in parallel to one another with the same pitch P and pass through the respective strata, from the front surfaces of the signal electrode layers 24d up to the front surface of the backing material 21.

Furthermore, an acoustic lens 28 is bonded onto the organic piezoelectric elements 25 through a protective layer 27.

The inorganic piezoelectric body 22a of the inorganic piezoelectric element 22 is formed of lead-based perovskite type oxide. For example, the inorganic piezoelectric body 22a can be formed of a lead-based piezoelectric ceramic represented by lead zirconate titanate ($Pb(Zr,Ti)O_3$) or a relaxor-type piezoelectric single crystal represented by a lead magnesium niobate-lead titanate solid solution (PMN-PT) and a lead zinc niobate-lead titanate solid solution (PZN-PT). Meanwhile, the upper organic layer 24a of the organic piezoelectric element 25 is formed of a vinylidene fluoride (VDF) material. For example, the upper organic layer 24a can be formed of a piezoelectric polymer, such as polyvinylidene fluoride (PVDF) or a polyvinylidene fluoride-trifluoroethylene copolymer (P(VDF-TrFE)).

The backing material 21 supports the inorganic piezoelectric elements 22 while absorbing ultrasonic waves emitted backwards. The backing material 21 can be formed of a rubber material, such as ferrite rubber.

The first acoustic matching layer 23 allows an ultrasonic beam from the inorganic piezoelectric elements 22 to efficiently enter into the subject, and is formed of a material having acoustic impedance of an intermediate value between the acoustic impedance of the inorganic piezoelectric elements 22 and the acoustic impedance of a living body.

The second acoustic matching layer 24 allows an ultrasonic beam from the inorganic piezoelectric elements 22 to efficiently enter into the subject. The lower organic layer 24b can be formed of a vinylidene fluoride (VDF) material, such as polyvinylidene fluoride (PVDF) or a polyvinylidene fluoride-trifluoroethylene copolymer (P(VDF-TrFE)), as is the case with the upper organic layer 24a. The upper organic layer 24a and the lower organic layer 24b are preferably formed of the materials which are identical or similar to each other in acoustic impedance. If the acoustic impedance of the upper organic layer 24a differs from that of the lower organic layer 24b by up to ±10%, for instance, it is possible to constitute the second acoustic matching layer 24 without affecting the acoustic matching of ultrasonic waves.

The filler which forms the separation parts 26 fixes the positions and postures of adjacent fragments, and is formed of, for example, epoxy resin or the like.

The protective layer 27 protects the ground electrode layer 24c of the organic piezoelectric element 25, and is formed of, for example, polyvinylidene fluoride (PVDF). If there is no trouble with respect to the protection of the ground electrode layer 24c, the formation of the protective layer 27 may be omitted, and the acoustic lens 28 may be directly bonded onto the organic piezoelectric elements 25.

The acoustic lens 28 focuses the ultrasonic beam using refraction to improve resolution in an elevation direction, and is formed of silicone rubber or the like.

Next, the operation of Embodiment 2 will be described.

During the operation, the inorganic piezoelectric elements 22 are used as transducers for both transmission and reception of ultrasonic waves, and the organic piezoelectric elements 25 are used as transducers exclusively for reception of ultrasonic waves.

When a pulsed or continuous-wave voltage is applied between the signal electrode layer 22b and the ground electrode layer 22c of each of the inorganic piezoelectric elements 22, the inorganic piezoelectric bodies 22a of the respective inorganic piezoelectric elements 22 expand and contract to generate pulsed or continuous-wave ultrasonic waves. These ultrasonic waves enter the subject through the first acoustic matching layer 23, the second acoustic matching layer 24, the protective layer 27, and the acoustic lens 28, and are combined with one another to form an ultrasonic beam, which propagates the inside of the subject.

Subsequently, when an ultrasonic echo, or the ultrasonic which has propagated and been reflected in the subject enters the respective organic piezoelectric elements 25 through the acoustic lens 28 and the protective layer 27, the upper organic layer 24a expands and contracts in response to the harmonic components of the ultrasonic waves with high sensitivity, and electrical signals are generated between the signal electrode layers 24d and the ground electrode layer 24c, and output as reception signals.

Furthermore, the ultrasonic echo transmitted through the organic piezoelectric elements 25 enters the respective inorganic piezoelectric elements 22 through the second acoustic matching layer 24 and the first acoustic matching layer 23. With this, the inorganic piezoelectric bodies 22a expand and contract in response to the fundamental components of the ultrasonic waves, and electrical signals are generated between the signal electrode layers 22b and the ground electrode layers 22c.

In this way, image data of the harmonic components can be generated based on the reception signals output from the organic piezoelectric elements 25, and image data of the fundamental components can be generated based on the reception signals from the inorganic piezoelectric elements 22. Frame correlation processing is performed on the image data of the fundamental components and the image data of the harmonic components to produce a correlation processing image of the fundamental components and a correlation processing image of the harmonic components, and then, the correlation processing image of the fundamental components and the correlation processing image of the harmonic components are added to each other, thereby producing a composite image in which the fundamental components and the harmonic components are combined.

Since the inorganic piezoelectric elements 22 and the organic piezoelectric elements 25 are aligned in the lamination direction and arranged with the same pitch P, it is possible to receive the fundamental components and the harmonic components in the same arrangement positions and to produce the composite image in which the fundamental components and the harmonic components are combined with high accuracy.

What is claimed is:

1. An ultrasound diagnostic apparatus, comprising:
   a transducer array having a plurality of inorganic piezoelectric elements and a plurality of organic piezoelectric elements;
   a transmission circuit configured to transmit an ultrasonic beam from the transducer array toward a subject;
   a reception circuit configured to obtain a plurality of frames of fundamental component data by processing reception signals corresponding to a fundamental component of an ultrasonic wave output from the inorganic piezoelectric elements, and obtain a plurality of frames of harmonic component data by processing reception signals corresponding to a harmonic component of the ultrasonic wave output from the organic piezoelectric elements, upon reception of an ultrasonic echo from the subject by the transducer array; and
   a processor configured to perform frame correlation processing on a frame of the fundamental component data generated by the reception circuit by using at least one other frame of the fundamental component data so as to produce a correlation processing image of the fundamental component, perform frame correlation processing on a frame of the harmonic component data generated by the reception circuit by using at least one other frame of the harmonic component data so as to produce a correlation processing image of the harmonic component, and add the correlation processing image of the fundamental component and the correlation processing image of the harmonic component to each other so as to produce an ultrasound image in which the fundamental component and the harmonic component are combined together,
   wherein the processor performs the frame correlation processing on the frame of the fundamental component data and the frame correlation processing on the frame of the harmonic component data such that weight of the at least one other frame of the harmonic component data used in the frame correlation processing of the harmonic component data is greater than weight of the at least one other frame of the fundamental component data used in the frame correlation processing of the fundamental component data.

2. The ultrasound diagnostic apparatus according to claim 1,
   wherein the fundamental component data is image data of the fundamental component that is generated based on the reception signals from the inorganic piezoelectric elements, and the harmonic component data is image data of the harmonic component that is generated based on the reception signals from the organic piezoelectric elements, and
   wherein the processor performs frame correlation processing on the image data of the fundamental component and the image data of the harmonic component so as to produce the correlation processing image of the fundamental component and the correlation processing image of the harmonic component.

3. The ultrasound diagnostic apparatus according to claim 1,
   wherein the processor performs the frame correlation processing on the fundamental component data and the harmonic component data such that a value of intensity of noise included in the correlation processing image of the harmonic component is comparable to a value of intensity of noise included in the correlation processing image of the fundamental component.

4. The ultrasound diagnostic apparatus according to claim 1,
   wherein the processor uses, in the frame correlation processing of the harmonic component data, a number of the at least one other frame of the harmonic component data larger than a number of the at least one other frame of which the fundamental component data used in the frame correlation processing of the fundamental component data.

5. The ultrasound diagnostic apparatus according to claim 1,
   wherein the processor sets a correlation coefficient for the at least one other frame of the harmonic component data used in the frame correlation processing of the harmonic component data at a higher value than a correlation coefficient set for the at least one other frame of the fundamental component data used in the frame correlation processing of the fundamental component data.

6. The ultrasound diagnostic apparatus according to claim 1,
   wherein the transmission circuit transmits an ultrasonic beam from the inorganic piezoelectric elements of the transducer array.

7. The ultrasound diagnostic apparatus according to claim 1,
wherein the transducer array is a laminated transducer array in which the inorganic piezoelectric elements and the organic piezoelectric elements are mutually laminated.

8. The ultrasound diagnostic apparatus according to claim 7,
wherein the organic piezoelectric elements and the inorganic piezoelectric elements are arrayed with identical pitch.

9. The ultrasound diagnostic apparatus according to claim 8,
wherein the organic piezoelectric elements include:
a first organic layer which extends over the organic piezoelectric elements;
a plurality of signal electrode layers for organic piezoelectric elements that are arrayed on a surface of the first organic layer facing the inorganic piezoelectric elements and are separated from one another; and
a common ground electrode layer for organic piezoelectric elements that is arranged on another surface of the first organic layer and extends over the organic piezoelectric elements.

10. The ultrasound diagnostic apparatus according to claim 9,
wherein the transducer array includes a plurality of first acoustic matching layers arranged on the inorganic piezoelectric elements, and a second acoustic matching layer arranged on the first acoustic matching layers, and
wherein the second acoustic matching layer is formed of a plurality of second organic layers arranged between the first acoustic matching layers and the signal electrode layers for organic piezoelectric elements, respectively, and the first organic layer.

11. The ultrasound diagnostic apparatus according to claim 10,
wherein the transducer array further has a plurality of separation parts so extending in a lamination direction in parallel to one another with identical pitch as to separate respective strata of the transducer array, from the signal electrode layers for organic piezoelectric elements up to the inorganic piezoelectric elements, into a plurality of fragments.

* * * * *